United States Patent
Schefczik

[11] Patent Number: 6,043,369
[45] Date of Patent: Mar. 28, 2000

[54] [1,3,4] TRIAZOLO [1,5-A] PYRIDINES

[75] Inventor: Ernst Schefczik, Ludwigshafen, Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/966,968

[22] Filed: Nov. 10, 1997

Related U.S. Application Data

[63] Continuation of application No. 08/592,311, Feb. 12, 1996, abandoned, which is a continuation of application No. PCT/EP94/02233, Jul. 7, 1994.

[30] Foreign Application Priority Data

Aug. 10, 1993 [DE] Germany ............................ 43 26 758

[51] Int. Cl.[7] .................................................. C07D 471/04
[52] U.S. Cl. ........................................... 546/119; 546/120
[58] Field of Search ..................... 546/119, 120

[56] References Cited

PUBLICATIONS

Geissler, et al., Preparation of substituted, etc CA 115:114513 1991

*Primary Examiner*—Patricia L. Morris

*Attorney, Agent, or Firm*—Oblon, Spivak, McClelland, Maier & Neustadt, P.C.

[57] ABSTRACT

Triazolopyridines of the formula

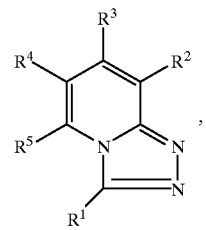

where $R^1$ is unsubstituted or substituted $C_1$–$C_{20}$-alkyl, unsubstituted or substituted phenyl or unsubstituted or substituted mercapto, $R^2$ is hydrogen, formyl, nitroso, cyano or substituted methyl, $R^3$ is unsubstituted or substituted $C_1$–$C_4$-alkyl, $C_1$–$C_4$-alkoxycarbonyl or phenyl, $R^4$ is hydrogen, cyano, carbamoyl, carboxyl or $C_1$–$C_4$-alkoxycarbonyl and $R^5$ is hydroxyl, mercapto, halogen, unsubstituted or substituted amino or the radical of a CH-acidic compound, and processes for preparing triazolopyridines are described.

8 Claims, No Drawings

[1,3,4] TRIAZOLO [1,5-A] PYRIDINES

This application is a Continuation of Ser. No. 08/592,311, filed on Feb. 12, 1996, abandoned, which is a 371 of International Application No. PCT/EP94/02233, filed on Jul. 7, 1994.

The present invention relates to novel triazolopyridines of the formula I

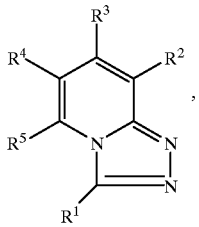
(I)

where $R^1$ is $C_1-C_{20}$-alkyl which is unsubstituted or substituted and can be interrupted by from 1 to 4 ether oxygen atoms, or is unsubstituted or substituted phenyl, mercapto or unsubstituted or substituted $C_1-C_{20}$-alkylthio, $R^2$ is hydrogen, formyl, nitroso, cyano, $C_1-C_4$-alkoxymethyl or a radical of the formula $CH_2-NL^1L^2$, where $L^1$ and $L^2$ are identical or different and independently of one another in each case are hydrogen or $C_1-C_4$-alkyl which may be interrupted by $C_1-C_4$-alkylimino, or together with the nitrogen bonding them are a 5- or 6-membered saturated heterocyclic radical, $R^3$ is $C_1-C_4$-alkyl which may be interrupted by an ether oxygen atom, or is $C_1-C_4$-alkoxycarbonyl or phenyl, $R^4$ is hydrogen, cyano, carbamoyl, carboxyl or $C_1-C_4$-alkoxycarbonyl and $R^5$ is hydroxyl, mercapto, halogen, the radical $-NL^1L^2$, where $L^1$ and $L^2$ in each case have the abovementioned meanings, or the radical of a CH-acidic compound, suitable CH-acidic compounds being nitromethane, nitroethane or compounds of the formulae VII to XII

(VII)

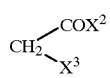
(VIII)

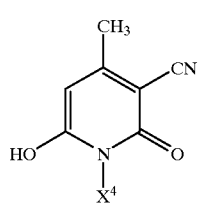
(IX)

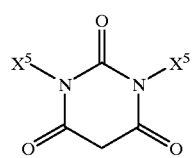
(X)

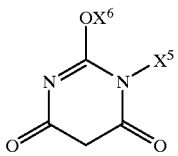
(XI)

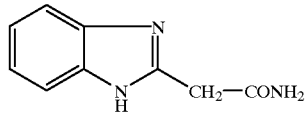
(XII)

where $X^1$ is cyano, nitro, $C_1-C_4$-alkanoyl, benzoyl which is unsubstituted or substituted by $C_1-C_4$-alkyl, $C_1-C_4$-alkoxy or halogen, $C_1-C_4$-alkylsulfonyl, or phenylsulfonyl, carboxyl, $C_1-C_4$-alkoxycarbonyl, phenoxycarbonyl, carbamoyl, $C_1-C_4$-monoalkylcarbamoyl or $C_1-C_4$-dialkylcarbamoyl, each of which is unsubstituted or substituted by $C_1-C_4$-alkyl, $C_1-C_4$-alkoxy or halogen, or phenylcarbamoyl which is unsubstituted or substituted by $C_1-C_4$-alkyl, $C_1-C_4$-alkoxy or halogen, or phenyl, benzothiazol-2-yl, benzimidazol-2-yl, 5-phenyl-1,3,4-thiadiazol-2-yl or 2-hydroxyquinoxalin-3-yl, each of which is unsubstituted or substituted by $C_1-C_4$-alkyl, $C_1-C_4$-alkoxy, halogen or nitro, $X^2$ is $C_1-C_4$-alkyl or $C_1-C_4$-alkoxy, $X^3$ is $C_1-C_4$-alkoxycarbonyl, phenylcarbamoyl or benzimidazol-2-yl, $X^4$ is hydrogen or $C_1-C_6$-alkyl, $X^5$ is hydrogen, $C_1-C_4$-alkyl or phenyl and $X^6$ is $C_1-C_4$-alkyl, and processes for preparing triazolopyridines.

U.S. Pat. No. 5,101,028 discloses [1,2,4]triazolo[1,5-a]pyridines.

It is an object of the present invention to prepare novel triazolopyridines having a different chemical structure. They should be simple to prepare.

We have found that this object is achieved by the triazolopyridines of the formula I described in greater detail at the beginning.

The exact IUPAC name of the basic structure on which the novel triazolopyridines of the formula I are based is [1,3,4]triazolo[1,5-a]pyridine, with the following numbering of the rings:

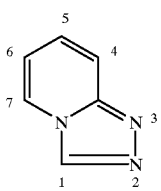

The compounds of the formula I can occur in several tautomeric forms which are all included by the patent claims. For example, the compounds where $R^5$=hydroxyl can occur, inter alia, in the following tautomeric forms:

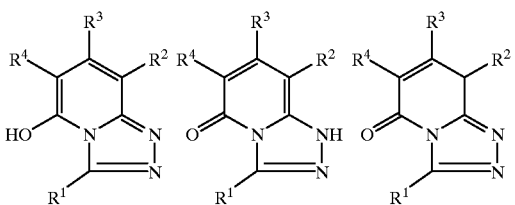

If substituted $C_1$–$C_{20}$-alkyl radicals occur in formula I, suitable substituents can be eg. unsubstituted or substituted phenyl, unsubstituted or substituted phenoxy, carboxyl or $C_1$–$C_{20}$-alkoxycarbonyl whose alkyl chain can be interrupted by from 1 to 4 ether oxygen atoms and can be substituted by phenyl or phenoxy. The alkyl radicals here as a rule have 1 or 2 substituents.

If alkyl radicals which are interrupted by ether oxygen atoms occur in the formula I, those alkyl radicals are preferred which are interrupted by 1 or 2 ether oxygen atoms.

If substituted phenyl radicals occur in the formula I, suitable substituents can be eg. $C_1$–$C_4$-alkyl, $C_1$–$C_4$-alkoxy, halogen, in this case in particular chlorine or bromine, or nitro or carboxyl. The phenyl radicals here as a rule have from 1 to 3 substituents.

If $R^5$ in formula I is a radical of a CH-acidic compound, particular mention should be made of CH-acidic compounds of the formula VII, VIII or X, where $X^1$ is cyano, acetyl, benzoyl, $C_1$–$C_4$-alkoxycarbonyl, phenoxycarbonyl, $C_1$–$C_2$-monoalkylcarbonyl, phenylcarbamoyl, phenyl, benzimidazol-2-yl, benzothiazol-2-yl or 5-phenyl-1,3,4-thiazol-2-yl, $X^2$ is $C_1$–$C_2$-alkoxy, $X^3$ is $C_1$–$C_2$-alkoxycarbonyl or phenylcarbamoyl and $X^5$ is methyl.

$R^1$ and $R^3$ radicals are eg. methyl, ethyl, propyl, isopropyl, butyl, isobutyl or sec-butyl.

$R^1$ radicals are furthermore eg. pentyl, isopentyl, neopentyl, tert-pentyl, hexyl, heptyl, 1-ethylpentyl, octyl, isooctyl, 2-ethylhexyl, nonyl, isononyl, decyl, isodecyl, undecyl, dodecyl, tridecyl, isotridecyl, tetradecyl, pentadecyl, hexadecyl, heptadecyl, octadecyl, nonadecyl, eicosyl (the above names isooctyl, isononyl, isodecyl and isotridecyl are trivial names and are derived from the alcohols obtained by oxo synthesis—cf. for this Ullmanns Enzyklopädie der technischen Chemie [Ullmann's Encyclopaedia of Industrial Chemistry], 4th edition, volume 7, pages 215 to 217, and volume 11, pages 435 and 436), 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 3,6,9-trioxadecyl, 3,6,9-trioxaundecyl, 3,6,9,12-tetraoxatridecyl, 3,6,9-trioxatetradecyl, 2-carboxyethyl, 2-methoxycarbonylethyl, benzyl, 1- or 2-phenylethyl, 2-, 3- or 4-methylbenzyl, 2-, 3- or 4-methoxybenzyl, 2-, 3- or 4-chlorobenzyl, 2-, 3- or 4-nitrobenzyl, 3-benzyloxypropyl, phenoxymethyl, 6-phenoxy-4-oxahexyl, 8-phenoxy-4-oxaoctyl, 2-, 3- or 4-methylphenyl, 2-, 3- or 4-methoxyphenyl, 2-, 3- or 4-chlorophenyl, 2-, 3- or 4-nitrophenyl, 2-, 3- or 4-carboxyphenyl, methylthio, ethylthio, propylthio, isopropylthio, butylthio, isobutylthio, sec-butylthio, pentylthio, isopentylthio, neopentylthio, tert-pentylthio, hexylthio, heptylthio, 1-ethylpentylthio, octylthio, isooctylthio, 2-ethylhexylthio, nonylthio, isononylthio, decylthio, isodecylthio, undecylthio, dodecylthio, tridecylthio, isotridecylthio, tetradecylthio, pentadecylthio, hexadecylthio, heptadecylthio, octadecylthio, nonadecylthio or eicosylthio.

$R^4$ radicals are eg. methoxycarbonyl, ethoxycarbonyl, propoxycarbonyl, isopropoxycarbonyl, butoxycarbonyl, isobutoxycarbonyl or sec-butoxycarbonyl.

$R^2$ radicals are eg. aminomethyl, N-mono- or N,N-dimethylaminomethyl, N-mono- or N,N-diethylaminomethyl, N-mono- or N,N-dipropylaminomethyl, pyrrolidinomethyl, piperidinomethyl, morpholinomethyl, piperazinomethyl, N-($C_1$–$C_4$-alkyl)piperazinomethyl, methoxymethyl, ethoxymethyl, propoxymethyl, isopropoxymethyl or butoxymethyl.

$R^3$ radicals are furthermore eg. methoxymethyl, ethoxymethyl, 2-methoxyethyl, 2-ethoxyethyl, methoxycarbonyl, ethoxycarbonyl, propoxycarbonyl or butoxycarbonyl.

$R^5$ radicals are eg. amino, mono- or dimethylamino, mono- or diethylamino, mono- or dipropylamino, mono- or diisopropylamino, mono- or dibutylamino, 2-dimethylaminoethylamino, 2- or 3-dimethylaminopropylamino, pyrrolidino, piperidino, morpholino, piperazino or N-($C_1$–$C_4$-alkyl) piperazino.

Preferred triazolopyridines of the formula I are those in which one of the two radicals $R^2$ and $R^4$ is hydrogen and the other is cyano.

Furthermore preferred triazolopyridines of the formula I are those in which $R^2$ is cyano.

Furthermore preferred triazolopyridines of the formula I are those in which $R^3$ is $C_1$–$C_4$-alkyl, in particular methyl.

Furthermore preferred triazolopyridines of the formula I are those in which $R^1$ is $C_1$–$C_{13}$-alkyl or phenyl.

Particularly preferred triazolopyridines of the formula I are those in which $R^2$ is cyano and $R^4$ is hydrogen.

It is a further object of the present invention to make available suitable processes by means of which it is possible to prepare specific triazolopyridines of the formula I in a simple manner and without great cost.

We have furthermore found that this object is achieved by the preparation of the triazolopyridines which correspond to the formula Ia

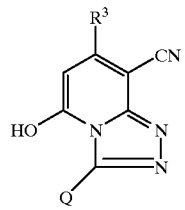

(Ia)

where Q is $C_1$–$C_{20}$-alkyl which is unsubstituted or substituted and can be interrupted by from 1 to 4 ether oxygen atoms, or is unsubstituted or substituted phenyl and $R^3$ has the abovementioned meanings, which proceeds advantageously if a dicarbonyl compound of the formula II $$R^3\text{—CO—CH}_2\text{—COOW} \qquad (II),$$

where W is $C_1$–$C_4$-alkyl and $R^3$ has the abovementioned meanings, is reacted with a cyanomethyltriazole of the formula III

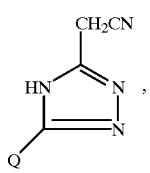

(III)

where Q has the abovementioned meanings, in the presence of a base and of a solvent at from 50 to 150° C.

Suitable bases are eg. alkali metal alkoxides, such as lithium methoxide or ethoxide, sodium methoxide or ethoxide or potassium methoxide or ethoxide, alkali metal amides, such as lithium amide, sodium amide or potassium amide, alkali metal hydrides, such as lithium hydride, sodium hydride or potassium hydride, or alkali metal hydroxides, such as lithium hydroxide, sodium hydroxide or potassium hydroxide.

Suitable solvents are eg. alcohols, such as methanol, ethanol, propanol, isopropanol, butanol, ethylene glycol, diethylene glycol or ethylene glycol monomethyl ether or ethylene glycol monoethyl ether, or N-methylpyrrolidone.

The molar ratio dicarbonyl compound II: cyanomethyltriazole III is in general from 1:1 to 3:1, preferably from 1:1 to 1.5:1.

From 1 to 2 mol of base are customarily used per mole of dicarbonyl compound II.

After completion of the reaction, which as a rule takes from 1 to 8 hours, the reaction mixture is diluted with water and neutralized by addition of acid, eg. concentrated hydrochloric acid. The target product of the formula Ia which is obtained as a precipitate during the course of this can then be separated off and further purified if desired.

We have furthermore found that the preparation of the triazolopyridines of the formula Ib

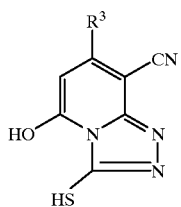

(Ib)

where $R^3$ has the abovementioned meanings, proceeds advantageously if a hydrazinopyridine of the formula IV

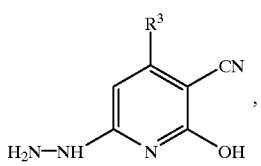

(IV)

where $R^3$ has the abovementioned meanings, is treated with carbon disulfide.

The treatment as a rule takes place at from 25 to 100° C. in the presence of pyridine. Pyridine is used in this case as the base and as the diluent. However, it is also possible to carry out the reaction in an alcohol, eg. methanol or ethanol, in the presence of a base, eg. lithium methoxide or ethoxide, sodium methoxide or ethoxide or potassium methoxide or ethoxide.

As a rule, from 1 to 10 mol, preferably from 1 to 5 mol, of carbon disulfide are used per mole of hydrazinopyridine IV.

From 1 to 10 parts by weight of pyridine are in general used per part by weight of hydrazinopyridine IV.

After completion of the reaction, which as a rule takes from 2 to 8 hours, the resulting reaction mixture is mixed with a diluent, eg. methanol, and the target product of the formula Ib obtained as a precipitate is isolated and further purified if desired.

We have furthermore found that the preparation of triazolopyridines of the formula Ic

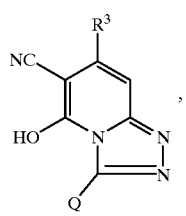

(Ic)

where Q and $R^3$ in each case have the abovementioned meanings, proceeds advantageously if a hydrazinopyridine of the abovementioned formula IV is acylated with a carboxylic acid derivative of the formula V

Q—CO—Y (V)

where Y is chlorine, bromine or the radical O—CO—Q and Q in each case has the abovementioned meanings, and the resulting acyl compound of the formula VI

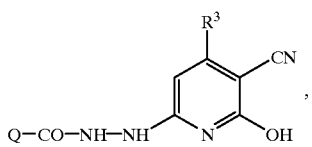

(VI)

where Q and $R^3$ in each case have the abovementioned meanings, is dehydrated with ring closure.

The acylation as a rule takes place at from 25 to 125° C. and in the presence of a solvent, eg. pyridine or quinoline.

As a rule, from 1 to 2 mol of carboxylic acid derivative V are used per mole of hydrazinopyridine IV.

The resulting acyl compound VI can either be initially isolated as an intermediate or directly converted to the target product of the formula Ic.

The dehydration as a rule takes place at from 80 to 150° C. and in the presence of a solvent, eg. N-methylpyrrolidone, N,N-dimethylformamide or N,N-dimethylacetamide, and also of a dehydrating agent.

A suitable dehydrating agent is eg. phosphorus pentoxide.

From 1 to 1.5 mol of dehydrating agent are in general used per mole of hydrazinopyridine IV.

After completion of the reaction, which in general takes from 0.5 to 4 hours, the reaction mixture is mixed with water. The target product of the formula Ic, which is present as a precipitate, can then be separated off and further purified if desired.

The other triazolopyridines of the formula I can be prepared from the compounds of the formula Ia, Ib or Ic by a route known per se.

For example, the substituent $R^2$ can be introduced by means of an electrophilic substitution reaction, eg. Vilsmeier reaction, or nitrosation, with or without subsequent derivatization.

The cyano group in position 4 or 6 can be converted by methods known per se to the carbamoyl, carboxyl or $C_1$–$C_4$-alkoxycarbonyl group.

By treatment with acid halides, in particular acid chlorides, eg. phosphorus oxychloride, the hydroxyl group in position 7 can be replaced by halogen.

The halogen atom can in turn be replaced by methods known per se by CH-acidic compounds, amines of the formula VII

(VII)

where $L^1$ and $L^2$ in each case have the abovementioned meanings, or hydrogen sulfide.

The mercapto compounds of the formula Ib can be converted to the respective alkylthio compounds by treatment with appropriate alkylating agents.

The novel triazolopyridines of the formula I are useful intermediates, in particular for the synthesis of dye-stuffs.

The following examples will illustrate the invention in greater detail.

EXAMPLE 1

150 g of 3-isopropyl-5-cyanomethyl-1,2,4-triazole were introduced into 250 g of ethyl acetoacetate and stirred at 75° C. under a descending condenser. 200 g of 30% strength methanolic sodium methoxide solution were allowed to run in and the temperature was increased to 115° C. Methanol distilled off during the course of this and the reaction mixture was converted into a crystal magma. After 6 hours, 500 ml of water and 200 ml of conc. hydrochloric acid were added, and the mixture was boiled briefly and allowed to cool. The precipitated product was then filtered off with suction, washed with water until neutral and dried at 75° C. under reduced pressure. 211 g of a colorless compound of the formula

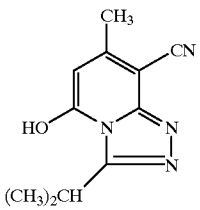

were obtained.

Melting point from 330 to 331° C. (from γ-butyrolactone); Analyses $C_{11}H_{12}N_4O$ (216);

| calc.: | C 61.1 | H 5.6 | N 25.9 | O 7.4 |
| --- | --- | --- | --- | --- |
| found: | C 61.0 | H 5.8 | N 25.6 | O 7.8 |

The triazolopyridines of the formula

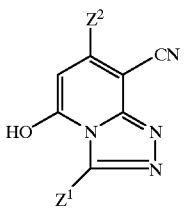

listed in Table 1 below are obtained in a similar manner.

TABLE 1

| Ex. No. | $Z^1$ | $Z^2$ | Yield % of theory | Melting point [°C.] | Empirical formula (molecular weight) | | C | H | N | O | Cl |
|---|---|---|---|---|---|---|---|---|---|---|---|
| 2 | $C_2H_5$ | $CH_3$ | 71 | 295–296 (N,N-dimethylformamide) | $C_{10}H_{10}N_4O$ (202) | calc.: found: | 59.4 59.1 | 5.0 5.1 | 27.7 27.4 | 7.9 8.4 | |
| 3 | $C_2H_5$ | $C_6H_5$ | 80 | 299–300 (γ-butyrolactone) | $C_{15}H_{12}N_4O$ (264) | calc.: found: | 68.2 67.9 | 4.6 4.5 | 21.2 20.8 | 6.1 6.5 | |
| 4 | $CH(CH_3)_2$ | $CH_2O$— $COOCH_3$ | 88 | 277–278 (pentanol) | $C_{12}H_{14}N_4O_2$ (246) | calc.: found: | 58.5 58.4 | 5.7 5.9 | 22.8 22.8 | 13.0 13.4 | |
| 5 | $CH(CH_3)_2$ | $CH_3$ | 53 | 277–278 (methanol) | $C_{12}H_{12}N_4O_3$ (260) | calc.: found: | 55.4 55.2 | 4.7 4.8 | 21.5 21.8 | 18.4 18.6 | |
| 6 | $CH(CH_3)_2$ | $C_6H_5$ | 55 | 325–327 (γ-butyrolactone) | $C_{16}H_{14}N_4O$ (278) | calc.: found: | 69.1 69.0 | 5.1 5.2 | 20.1 19.9 | 5.8 6.1 | |
| 7 | $CH_2CH_2OCH_3$ | $CH_3$ | 58 | 264–265 (acetic acid) | $C_{11}H_{12}N_4O_2$ (232) | calc.: found: | 56.9 57.1 | 5.2 5.1 | 24.1 23.8 | 13.8 14.1 | |
| 8 | $CH_2CH_2OCH_3$ | $C_6H_5$ | 63 | 173–174 (pentanol) | $C_{16}H_{14}N_4O_2$ (294) | calc.: found: | 65.3 65.0 | 4.8 5.0 | 19.0 18.7 | 10.9 11.3 | |
| 9 | $CH_2CH_2OC_3H_7$ | $CH_3$ | 32 | 248–249 (ethanol) | $C_{13}H_{16}N_4O_2$ (260) | calc.: found: | 60.0 59.7 | 6.2 6.3 | 21.5 21.3 | 12.3 12.3 | |
| 10 | $CH_2CH_2COOH$ | $CH_3$ | 68 | 300–301 (acetic acid) | $C_{11}H_{10}N_4O_3$ (246) | calc.: found: | 53.6 53.3 | 4.1 4.2 | 22.8 22.8 | 19.5 19.7 | |
| 11 | $CH_2C_6H_5$ | $CH_3$ | 91 | 324–325 (γ-butyrolactone) | $C_{15}H_{12}N_4O$ (264) | calc.: found: | 68.2 68.0 | 4.6 4.7 | 21.2 21.0 | 6.1 6.5 | |
| 12 | $CH_2COOC_2H_5$ | $CH_3$ | 46 | 221–222 (acetic acid) | $C_{12}H_{12}N_4O_3$ (260) | calc.: found: | 55.4 55.5 | 4.7 4.8 | 21.5 21.5 | 18.4 18.6 | |
| 13 | 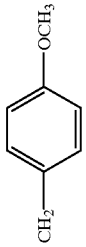 | $CH_3$ | 93 | 332–333 (N,N-dimethylformamide) | $C_{16}H_{14}N_4O$ (278) | calc.: found: | 69.0 69.0 | 5.1 5.3 | 20.1 20.3 | 5.98 6.0 | |
| 14 | | $CH_3$ | 97 | 293–294 (N,N-dimethylformamide) | $C_{16}H_{14}N_4O_2$ (294) | calc.: found: | 65.3 65.0 | 4.8 4.9 | 19.0 19.8 | 10.9 11.1 | |

TABLE 1-continued

| Ex. No. | Z¹ | Z² | Yield % of theory | Melting point [°C.] | Empirical formula (molecular weight) | | C | H | N | O | Cl |
|---|---|---|---|---|---|---|---|---|---|---|---|
| 15 | 3-Cl-C$_6$H$_4$-CH$_2$ | CH$_3$ | 82 | 298–299 (N,N-dimethylformamide) | C$_{15}$H$_{11}$N$_4$OCl (298.5) | calc.: found: | | | | | 11.9 12.0 |
| 16 | 4-NO$_2$-C$_6$H$_4$-CH$_2$ | CH$_3$ | 99 | 340 (N,N-dimethylformamide) | C$_{15}$H$_{11}$N$_5$O$_3$ (309) | calc.: found: | 58.2 58.0 | 3.6 3.8 | 22.6 22.5 | 15.5 15.9 | |
| 17 | C$_6$H$_5$ | CH$_3$ | 98 | 337–338 (N,N-dimethylformamide) | C$_{14}$H$_{10}$N$_4$O (250) | calc.: found: | 67.2 66.9 | 4.0 4.2 | 22.4 22.3 | 6.4 6.8 | |
| 18 | C$_6$H$_5$ | CH$_2$OCH$_3$ | 95 | 282–283 (γ-butyrolactone) | C$_{15}$H$_{12}$N$_4$O$_2$ (280) | calc.: found: | 64.3 64.1 | 4.3 4.4 | 20.0 19.8 | 11.4 11.8 | |
| 19 | C$_6$H$_5$ | C$_6$H$_5$ | 63 | 354–355 (N-methylpyrrolidone) | C$_{19}$H$_{12}$N$_4$O (312) | calc.: found: | 73.1 72.8 | 3.9 4.0 | 17.9 17.8 | 5.1 5.5 | |
| 20 | # | CH$_3$ | 98 | 330–331 (γ-butyrolactone) | C$_{15}$H$_{12}$N$_4$O (264) | calc.: found: | 68.2 68.0 | 4.5 4.5 | 21.2 21.0 | 6.1 6.5 | |

EXAMPLE 21

20.2 g of the compound obtained according to Example 2 were introduced into 80 ml of conc. sulphuric acid and the mixture was stirred at 75° C. for 4 hours. The product was precipitated on ice, filtered off with suction and washed with 5% strength by weight hydrochloric acid. After drying, 16.8 g of the compound of the formula

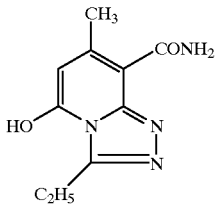

with a melting point of from 257 to 258° C. (from γ-butyrolactone) were obtained. The IR spectrum did not show a nitrile band.

EXAMPLE 22

250 g of the compound obtained according to Example 17 were introduced into 1500 ml of chloroform and 120 g of N,N-dimethylformamide and 250 g of phosphorus oxychloride were then added dropwise with stirring. In the course of this, the mixture heated to boiling. It was heated under reflux for a further 6 hours, 500 ml of water were added and the solvent was removed by steam distillation. The remaining suspension was filtered off with suction, and the product was washed with water and dried at 100° C. 268 g of the compound of the formula

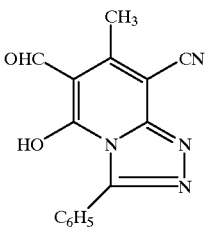

were obtained. A sample recrystallized from N,N-dimethylformamide melts at from 274 to 276° C. and has the following analysis: $C_{15}H_{10}N_4O_2$ (278);

| | | | | |
|---|---|---|---|---|
| calc.: | C 64.7 | H 3.6 | N 20.1 | O 11.5 |
| found: | C 64.4 | H 3.7 | N 19.8 | O 11.9 |

The compounds of the formula

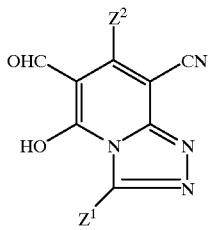

listed in Table 2 below are obtained in a similar manner to Example 22.

TABLE 2

| Ex. No. | $Z^1$ | $Z^2$ | Yield % of theory | Melting point [° C.] | Empirical formula (molecular weight) | | C | H | N | O |
|---|---|---|---|---|---|---|---|---|---|---|
| 23 | $C_2H_5$ | $CH_3$ | 73 | 235–236° (pentanol) | $C_{11}H_{10}N_4O_2$ (230) | calc.: found: | 57.4 57.5 | 4.4 4.7 | 24.3 24.5 | 13.9 13.6 |
| 24 | $CH(CH_3)_2$ | $CH_3$ | 90 | 255 (γ-butyrolactone) | $C_{25}H_{12}N_4O_2$ (244) | calc.: found: | 59.0 58.9 | 5.0 5.0 | 22.9 22.7 | 13.1 13.5 |
| 25 | $CH_2CH_2OCH_3$ | $CH_3$ | 63 | 179–180 (butanol) | $C_{12}H_{12}N_4O_3$ (260) | calc.: found: | 55.4 55.3 | 4.6 4.6 | 21.5 21.4 | 18.5 18.8 |
| 26 | $CH_2C_6H_5$ | $CH_3$ | 97 | 245–246 (acetic acid) | $C_{16}H_{12}N_4O_2$ (292) | | 65.7 65.3 | 4.1 4.3 | 19.2 18.9 | 11.0 11.4 |

EXAMPLE 27

250 g of the compound obtained according to Example 17 were introduced into 600 g of phosphorus oxychloride and the mixture was heated under reflux for 6 hours. Excess phosphorus oxychloride was then stripped off under reduced pressure, 1000 ml of ethanol were added dropwise to the residue and the mixture was heated for 1 hour. After cooling, the solid was filtered off with suction, washed with methanol and dried at 50° C. under reduced pressure. 247 g of the compound of the formula

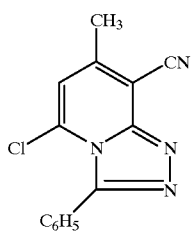

were obtained in the form of colorless crystals of melting point from 223 to 224° C. (from acetic acid).

$C_{14}H_9ClN_4$ (268.5) calc. Cl 13.2, found Cl 13.3.

The compounds of the formula

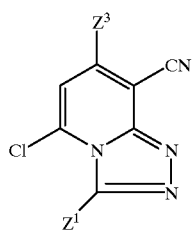

listed in Table 3 below are obtained in a similar manner to Example 27.

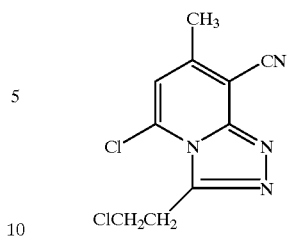

having a melting point of from 135 to 136° C. (from ethanol) were obtained.

$C_{10}H_8Cl_2N_4$ (255) calc. Cl 27.8, found Cl 27.6.

TABLE 3

| Ex. No. | $Z^1$ | $Z^2$ | Yield % of theory | Melting point [° C.] | Empirical formula (molecular weight) | Cl calc. | Cl found |
|---|---|---|---|---|---|---|---|
| 28 | $CH(CH_3)_2$ | $CH_3$ | 94 | 154–155 (ethanol) | $C_{11}H_{11}ClN_4$ (234.5) | 15.1 | 15.0 |
| 29 | $CH_2C_6H_5$ | $CH_3$ | 91 | 178–179 (pentanol) | $C_{15}H_{11}ClN_4$ (282.5) | 12.6 | 12.5 |
| 30 | $CH_2$-(2-methylphenyl) | $CH_3$ | 84 | 196–197 (acetic acid) | $C_{16}H_{13}ClN_4$ (296.5) | 12.0 | 11.8 |
| 31 | $CH_2$-(4-methoxyphenyl) | $CH_3$ | 81 | 166–167 (acetic acid) | $C_{16}H_{13}ClN_4O$ (312.5) | 11.4 | 11.1 |
| 32 | $CH_2$-(3-chlorophenyl) | $CH_3$ | 75 | 152–153 (ethanol) | $C_{15}H_{10}Cl_2N_4$ (317) | 22.4 | 22.1 |
| 33 | 4-methoxyphenyl | $CH_3$ | 94 | 227–228 (acetic acid) | $C_{15}H_{11}ClN_4O$ (298.5) | 11.9 | 11.6 |
| 34 | 4-methylphenyl | $CH_3$ | 79 | 209–210 (acetic acid) | $C_{15}H_{11}ClN_4$ (282.5) | 12..6 | 12.5 |
| 35 | $C_6H_5$ | $CH_2OCH_3$ | 61 | 174–175 (acetic acid) | $C_{15}H_{11}ClN_4O$ (298.5) | 11.9 | 11.8 |

EXAMPLE 36

232 g of the compound obtained according to Example 7 were introduced into 500 g of phosphorus oxychloride and the mixture was heated under reflux for 6 hours. After working up, as described in Example 27, 193 g of the compound of the formula

EXAMPLE 37

234.5 g of the compound obtained according to Example 28 were introduced into a mixture of 1000 ml of ethanol, 200 g of diethylamine and 300 ml of water and the mixture was heated under reflux for 4 hours. Half of the solvent was then removed by distillation, 500 ml of water were added and the mixture was allowed to cool, the reaction product crystallizing out in the course of this. After filtering off with suction and drying at 50° C. under reduced pressure, 236 g of the compound of the formula

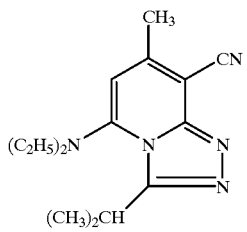

having a melting point of from 94 to 95° C. (from cyclohexane) were obtained.

$C_{15}H_{21}N_5$ (271).

| | | | |
|---|---|---|---|
| calc.: | C 66.4 | H 7.8 | N 25.8 |
| found: | C 66.5 | H 7.9 | N 25.9 |

The compounds of the formula

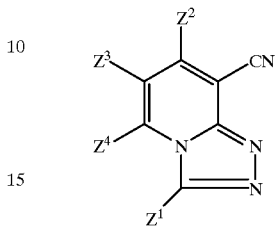

listed in Table 4 below are obtained in a similar manner to Example 37.

TABLE 4

| Ex. No. | $Z^1$ | $Z^2$ | $Z^3$ | $Z^4$ | Yield % of theory | Melting point [° C.] | Empirical formula (molecular weight) | N calc. | N found |
|---|---|---|---|---|---|---|---|---|---|
| 38 | $CH(CH_3)_2$ | $CH_3$ | H | $C_2H_5$ | 99 | 202–203 (pentanol) | $C_{13}H_{17}N_5$ (243) | 28.8 | 28.6 |
| 39 | $CH(CH_3)_2$ | $CH_3$ | H | $CH_2CH_2OH$ | 98 | 175–176 (ethanol) | $C_{13}H_{17}N_5O$ (259) | 27.0 | 26.9 |
| 40 | $CH(CH_3)_2$ | $CH_3$ | H | $(CH_2)_3N(CH_3)_2$ | 96 | 134–135 (toluene) | $C_{16}H_{24}N_6$ (300) | 28.0 | 28.3 |
| 41 | $CH(CH_3)_2$ | $CH_3$ | H | $C_4H_9$ | 99 | 103–104 (methanol) | $C_{15}H_{21}N_5$ (271) | 27.8 | 27.6 |
| 42 | $CH(CH_3)_2$ | $CH_3$ | H | $CH_2CH(C_2H_5)(C_4H_9)$ | 95 | 74–75 (cyclohexane) | $C_{19}H_{29}N_5$ (327) | 21.4 | 21.3 |
| 43 | $CH(CH_3)_2$ | $CH_3$ | $CH_3$ | $CH_3$ | 98 | 166–167 (ethanol) | $C_{13}H_{17}N_5$ (243) | 28.8 | 28.5 |
| 44 | $CH(CH_3)_2$ | $CH_3$ | $C_4H_9$ | $C_4H_9$ | 97 | 103–104 (methanol) | $C_{19}H_{29}N_5$ (327) | 21.4 | 21.2 |
| 45 | $CH(CH_3)_2$ | $CH_3$ | $CH_2CH_2OCH_2CH_2$ | | 99 | 178–179 (ethanol) | $C_{15}H_{19}N_5O$ (285) | 24.6 | 24.4 |
| 46 | $CH(CH_3)_2$ | $CH_3$ | $(CH_2)_5$ | | 96 | 92–93 (cyclohexane) | $C_{16}H_{21}N_5$ (283) | 24.8 | 24.7 |
| 47 | $C_6H_5$ | $CH_3$ | H | $(CH_2)_3OCH_3$ | 97 | 182–183 (butanol) | $C_{19}H_{19}N_5O$ (321) | 21.8 | 22.0 |
| 48 | $C_6H_5$ | $CH_3$ | H | $(CH_2)_3N(CH_3)_2$ | 97 | 185–186 (butanol) | $C_{19}H_{22}N_6$ (334) | 25.2 | 25.0 |
| 49 | $C_6H_5$ | $CH_3$ | $C_4H_9$ | $C_4H_9$ | 95 | 147–148 (ethanol) | $C_{22}H_{27}N_5$ (361) | 19.4 | 19.3 |
| 50 | $C_6H_5$ | $CH_2OCH_3$ | H | $(CH_2)_3N(CH_3)_2$ | 94 | 189–190 (butanol) | $C_{20}H_{24}N_6O$ (364) | 23.1 | 22.8 |
| 51 | 4-$OCH_3$-$C_6H_4$ | $CH_3$ | $C_2H_5$ | $C_2H_5$ | 87 | 169–170 (ethanol) | $C_{19}H_{21}N_5O$ (335) | 20.9 | 20.7 |
| 52 | 4-$CH_3$-$C_6H_4$ | $CH_3$ | H | $C_2H_5$ | 96 | 208–209 (pentanol) | $C_{17}H_{17}N_5$ (291) | 24.0 | 23.9 |

TABLE 4-continued

| Ex. No. | $Z^1$ | $Z^2$ | $Z^3$ | $Z^4$ | Yield % of theory | Melting point [° C.] | Empirical formula (molecular weight) | N calc. | N found |
|---|---|---|---|---|---|---|---|---|---|
| 53 | 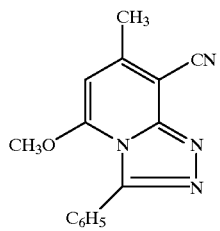 | $CH_3$ | $C_2H_5$ | $C_2H_5$ | 95 | 190–191 (pentanol) | $C_{19}H_{21}N_5$ (319) | 22.0 | 22.2 |

EXAMPLE 54

268.5 g of the compound obtained according to Example 27 were introduced into a solution of 75 g of sodium methoxide in 2000 ml of methanol and the mixture was heated under reflux for 8 hours. It was then poured onto water and the precipitated compound was filtered off with suction and washed with water. After drying, 260 g of the compound of the formula

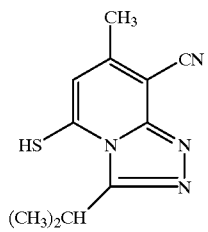

having a melting point of from 230 to 231° C. (from acetic acid) were obtained.

EXAMPLE 55

120 g of triethylamine and 234.5 g of the compound obtained according to Example 28 were introduced into 1500 ml of 1-methoxypropan-2-ol. Gaseous hydrogen sulfide was passed into the mixture and the temperature was raised to 100° C. in the course of an hour. After 4 hours, the mixture was precipitated in water and excess hydrochloric acid, and the product was filtered off with suction. After washing with water and drying, 218.8 g of the compound of the formula

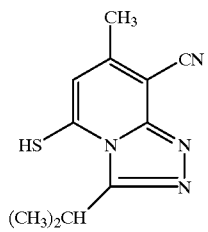

having a melting point of from 254 to 255° C. (from γ-butyrolactone/acetic acid) were obtained.

$C_{11}H_{12}N_4S$ (232);

| calc.: | C 56.9 | H 5.2 | N 24.1 | S 13.8 |
| found: | C 57.0 | H 5.2 | N 24.0 | S 13.7 |

EXAMPLE 56

130 g of ethyl mercaptoacetate and 234.5 g of the compound obtained according to Example 28 were introduced into 1500 ml of abs. ethanol and the mixture was stirred at room temperature. 120 g of triethylamine were allowed to run into this mixture, the temperature rising to 50° C. The mixture was heated under reflux for 2 hours and the clear solution was allowed to cool. The reaction product crystallized out during the course of this. The crystallization was completed by addition of 1200 ml of water and the reaction product was filtered off with suction, washed with water and dried at 70° C. under reduced pressure. 302 g of colorless crystals of the compound of the formula

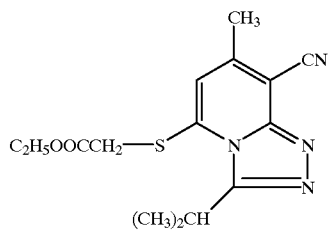

of melting point from 139 to 140° C. (from ethanol) were obtained.

$C_{15}H_{18}N_4O_2S$ (318): calc. S, 10.0, found S, 9.8.

EXAMPLE 57

Ethyl mercaptoacetate was replaced in Example 56 by 90 g of 2-mercaptoethanol and the procedure was otherwise as described in Example 56. 167 g of the compound of the formula

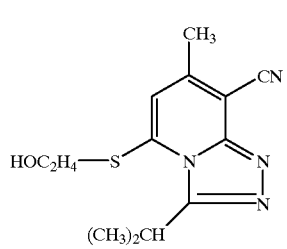

having a melting point of from 166 to 167° C. (from propanol) were obtained.

$C_{15}H_{16}N_4OS$ (276): calc. S, 11.6, found S, 11.5.

EXAMPLE 58

15 g of malononitrile were treated with 25 g of triethylamine in 200 ml of N,N-dimethylformamide at below 20° C. 23.5 g of the compound obtained according to Example 28 were added to this mixture. It was stirred at 90° C. for 6 hours, poured into 400 ml of water and adjusted to a pH of 3 by adding hydrochloric acid. The precipitated reaction product was then filtered off with suction, washed with water and dried at 100° C. 25.1 g of the compound of the formula

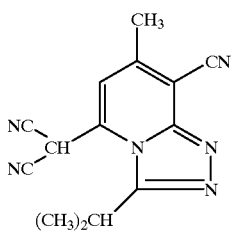

having a melting point of from 328 to 330° C. (from N,N-dimethylformamide/acetic acid) were obtained.

$C_{14}H_{12}N_6$ (264);

| calc.: | C 63.6 | H 4.6 | N 31.8 |
|---|---|---|---|
| found: | C 63.4 | H 4.8 | N 31.5 |

EXAMPLE 59

164 g of 2-hydroxy-3-cyano-4-methyl-6-hydrazinopyridine were stirred at 70° C. in 1000 ml of pyridine and treated with 192 g of the compound of the formula $(CH_3)_3C(CH_2)_5COCl$. The mixture was heated under reflux for 6 hours and the solution was poured onto 3000 g of ice and 1200 g of conc. hydrochloric acid. The precipitated product was filtered off with suction, washed with water and dried at 100° C. 288 g of the compound of the formula

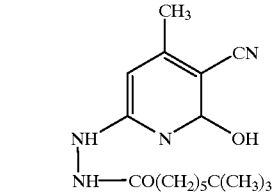

were obtained. A sample recrystallized from ethanol melts at from 285 to 286° C. and has the following analytical values:

$C_{17}H_{26}N_4O_2$ (318);

| calc.: | C 64.1 | H 8.2 | N 17.6 | O 10.00 |
|---|---|---|---|---|
| found: | C 64.0 | H 8.4 | N 17.6 | O 10.00 |

The compounds of the formula

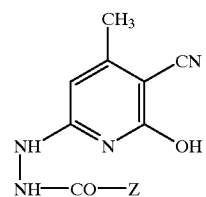

listed in Table 5 below are obtained in a similar manner to Example 59.

TABLE 5

| Ex. No. | Z | Yield % of theory | Melting point [° C.] | Empirical formula (molecular weight) | | C | H | N | O |
|---|---|---|---|---|---|---|---|---|---|
| 60 | $C_2H_5$ | 91 | 297–298 (γ-butyrolactone) | $C_{10}H_{12}N_4O_2$ (220) | calc.: found: | 54.6 54.6 | 5.5 5.7 | 25.5 25.2 | 14.5 14.6 |
| 61 | $C_3H_7$ | 61 | 275–276 (acetic acid) | $C_{11}H_{14}N_4O_2$ (234) | calc.: found: | 56.4 56.3 | 6.0 6.2 | 24.0 24.0 | 13.7 14.1 |
| 62 | $C_4H_9$ | 92 | 235–236 (pentanol) | $C_{12}H_{16}N_4O_2$ (248) | calc.: found: | 58.0 57.7 | 6.5 6.6 | 22.6 22.5 | 12.9 13.3 |
| 63 | $C(CH_3)_3$ | 97 | 293–294 (ethanol) | $C_{12}H_{18}N_4O_3$* (266) | calc.: found: | 54.2 54.0 | 6.8 6.9 | 21.0 21.3 | 18.0 17.8 |
| 64 | CH(C_2H_5)(C_4H_9) | 96 | 310–311 (acetic acid) | $C_{15}H_{22}N_4O_2$ (290) | calc.: found: | 62.1 61.9 | 7.6 7.7 | 19.3 19.3 | 11.0 11.1 |
| 65 | $C_6H_5$ | 97 | 322–324 (γ-butyrolactone) | $C_{14}H_{12}N_4O_2$ (268) | calc.: found: | 62.8 62.5 | 4.5 4.6 | 20.8 20.8 | 11.9 12.1 |

*crystallises with 1 mol of water of crystallization

General procedure for ring closure of the acylated hydrazinopyridines 1 mol of acylated hydrazinopyridine is stirred at from 80 to 100° C. in 2.5 times the amount of N-methylpyrrolidone and treated in portions with 1.1 mol of phosphorus pentoxide. The mixture is stirred at 125° C. for 4 hours, and the product is precipitated in water, filtered off with suction, washed with water until neutral and dried at 100° C.

The compounds of the formula

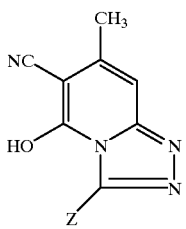

obtained according to the above procedure are listed in Table 6 below.

TABLE 6

| Ex. No. | Z | Yield % of theory | Melting point [° C.] | Empirical formula (molecular weight) | | C | H | N | O |
|---|---|---|---|---|---|---|---|---|---|
| 66 | C$_2$H$_5$ | 92 | 271–272 (pentanol) | C$_{10}$H$_{10}$N$_4$O (202) | calc.: found: | | | | |
| 67 | C$_3$H$_7$ | 93 | 271–272 (acetic acid) | C$_{11}$H$_{12}$N$_4$O (216) | calc.: found: | 61.1 61.0 | 5.6 5.8 | 25.9 25.6 | 7.4 7.8 |
| 68 | C$_4$H$_9$ | 86 | 260–261 (acetic acid) | C$_{12}$H$_{14}$N$_4$O (230) | calc.: found: | 62.6 62.3 | 6.1 6.3 | 24.3 24.3 | 7.0 7.2 |
| 69 | C(CH$_3$)$_3$ | 79 | >350 (γ-butyrolactone) | C$_{12}$H$_{14}$N$_4$O (230) | calc.: found: | 62.6 62.4 | 6.1 6.4 | 24.3 24.3 | 7.0 7.3 |
| 70 | CH(C$_2$H$_5$)(C$_4$H$_9$) | 92 | 245–246 (acetic acid) | C$_{15}$H$_{20}$N$_4$O (272) | calc.: found: | 66.1 66.4 | 7.4 7.4 | 20.6 20.9 | 5.9 5.9 |
| 71 | (CH$_2$)$_5$C(CH$_3$)$_3$ | 97 | 201–202 (ethanol) | C$_{17}$H$_{24}$N$_4$O (300) | calc.: found: | 68.0 67.7 | 8.1 8.3 | 18.6 18.6 | 5.3 5.7 |
| 72 | C$_6$H$_5$ | 93 | >350 (γ-butyrolactone) | C$_{14}$H$_{10}$N$_4$O (250) | calc.: found: | 67.2 67.4 | 4.0 4.0 | 22.4 22.6 | 6.4 6.7 |

EXAMPLE 73

164 g of 2-hydroxy-3-cyano-4-methyl-6-hydrazinopyridine were introduced into 1000 ml of pyridine and the mixture was stirred at 70° C. 104 g of succinic anhydride were added in portions and the reaction mixture was then heated under reflux for 6 hours. It was then precipitated on ice and excess hydrochloric acid, and the precipitated product was filtered off with suction and washed with water. After drying, 210 g of the compound of the formula

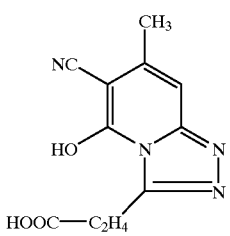

were obtained. The compound is soluble in aqueous ammonia. A sample recrystallized from γ-butyrolactone/acetic acid melts at from 329 to 330° C. and has the following analysis:

C$_{11}$H$_{10}$N$_4$O$_3$ (246);

| | | | | |
|---|---|---|---|---|
| calc.: | C 53.7 | H 4.1 | N 22.7 | O 19.5 |
| found: | C 53.9 | H 4.5 | N 22.4 | O 19.5 |

EXAMPLE 74

Succinic anhydride in Example 74 was replaced by 250 g of isobutyroyl chloride and the procedure was otherwise as described in Example 73. 179 g of the compound of the formula

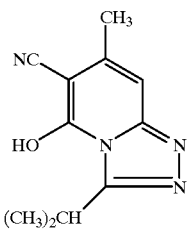

were obtained.

Melting point from 345 to 347° C. (from ethanol). C$_{11}$H$_{12}$N$_4$O (216);

| | | | | |
|---|---|---|---|---|
| calc.: | C 61.1 | H 5.6 | N 25.9 | O 7.4 |
| found: | C 60.8 | H 5.8 | N 26.0 | O 7.6 |

EXAMPLE 75

12 g of N,N-dimethylformamide and 27.2 g of the compound obtained according to Example 70 were introduced into 100 ml of chloroform and the mixture was stirred. 25 g of phosphorus oxychloride were added dropwise and the mixture was heated under reflux for 6 hours. The chloroform was then removed by steam distillation and the residual crystal suspension was filtered off with suction.

After drying at 100° C., 28.4 g of the compound of the formula

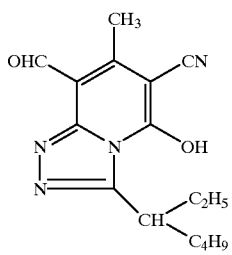

were obtained in the form of slightly yellowish crystals; melting point from 183 to 184° C. (from ethanol).

$C_{16}H_{20}N_4O_2$ (300);

| calc.: | C 64.0 | H 6.7 | N 18.7 | O 10.7 |
|---|---|---|---|---|
| found: | C 63.7 | H 6.8 | N 18.6 | O 11.0 |

EXAMPLE 76

30 g of carbon disulfide and 16.4 g of 2-hydroxy-3-cyano-4-methyl-6-hydrazinopyridine were introduced into 100 ml of pyridine and the mixture was stirred at 60° C. for 6 hours. The crystal suspension was diluted with 100 ml of methanol, filtered off with suction and washed with water. After drying, 24.9 g of the compound of the formula

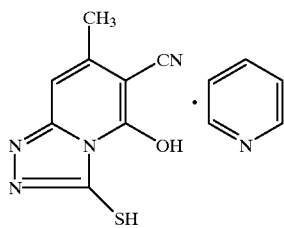

having a melting point of from 220 to 221° C., were obtained.

$C_{13}H_{11}N_5OS$ (285);

| calc.: | N 24.5 | S 11.2 |
|---|---|---|
| found: | N 24.2 | S 10.9 |

EXAMPLE 77

25 g of 20% strength by weight of sodium hydroxide solution were poured into a mixture of 200 ml of ethanol, 20 g of carbon disulfide and 16.4 g of 2-hydroxy-3-cyano-4-methyl-6-hydrazinopyridine. After heating under reflux for 2 hours, 100 ml of water and 20 g of n-butyl bromide were added and the mixture was stirred at 50° C. for a further 2 hours. It was then rendered neutral with acetic acid, and the precipitate was filtered off with suction and washed with water. After drying, 23.9 g of the compound of the formula

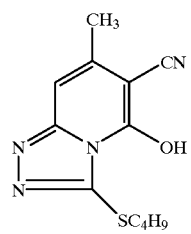

were obtained in the form of yellowish crystals; melting point from 277 to 278° C. (from pentanol).

$C_{12}H_{14}N_4OS$ (262);

| calc.: | C 54.9 | H 5.4 | N 21.4 | O 6.1 | S 12.2 |
|---|---|---|---|---|---|
| found: | C 54.9 | H 5.5 | N 21.5 | O 6.3 | S 12.0 |

The compounds of the formula

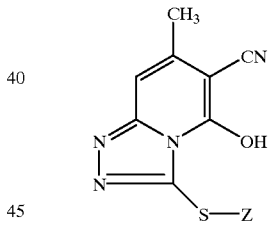

listed in Table 7 below are obtained in a similar manner to Example 77.

TABLE 7

| Ex. No. | Z | Yield % of theory | Melting point [° C.] | Empirical formula (molecular weight) | N calc. | N found | S calc. | S found |
|---|---|---|---|---|---|---|---|---|
| 78 | CH(CH₃)CH₃ | 89 | 293–294 (acetic acid) | $C_{11}H_{12}N_4OS$ (248) | 22.6 | 22.9 | 12.9 | 12.6 |
| 79 | CH₂CH(C₂H₅)C₄H₉ | 93 | 282–283 (ethanol) | $C_{16}H_{22}N_4OS$ (318) | 17.6 | 17.9 | 10.1 | 10.1 |

TABLE 7-continued

| Ex. No. | Z | Yield % of theory | Melting point [° C.] | Empirical formula (molecular weight) | N calc. | N found | S calc. | S found |
|---|---|---|---|---|---|---|---|---|
| 80 | CH$_2$COOCH(CH$_3$)CH$_3$ | 79 | 273–274 (N,N-dimethylformamide) | C$_{13}$H$_{14}$N$_4$O$_3$S (306) | 18.3 | 18.5 | 10.5 | 10.3 |
| 81 | CH$_2$COO(CH$_2$)$_2$OC$_4$H$_9$ | 80 | 254–255 (acetic acid) | C$_{16}$H$_{20}$N$_4$O$_4$S (364) | 15.4 | 15.2 | 8.8 | 8.8 |
| 82 | CH$_2$COOCH$_2$CH(C$_2$H$_5$)C$_4$H$_9$ | 69 | 263–264 (acetic acid) | C$_{18}$H$_{24}$N$_4$O$_3$S (376) | 14.9 | 14.8 | 8.5 | 8.4 |

We claim:

1. A triazolopyridine of the formula I

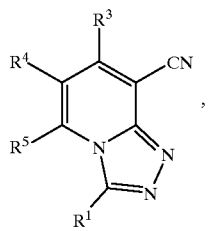

where $R^1$ is $C_1$–$C_{20}$-alkyl which can be interrupted by from 1 to 4 ether oxygen atoms, or is phenyl, mercapto or $C_1$–$C_{20}$-alkylthio, $R^3$ is $C_1$–$C_4$-alkyl which may be interrupted by an ether oxygen atom, or is $C_1$–$C_4$-alkoxycarbonyl or phenyl, $R^4$ is hydrogen, cyano, carbamoyl, carboxyl or $C_1$–$C_4$-alkoxycarbonyl and $R^5$ is hydroxyl, mercapto, halogen, the radical —NL$^1$L$^2$, where L$^1$ and L$^2$ are identical or different and independently of one another in each case are hydrogen or $C_1$–$C_4$-alkyl which may be interrupted by $C_1$–$C_4$-alkylimino, or the radical nitromethane, nitroethane or compounds of the formulae VII to VIII

 (VII)

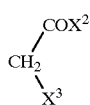 (VIII)

where $X^1$ is cyano, nitro, $C_1$–$C_4$-alkanoyl, benzoyl which is unsubstituted or substituted by $C_1$–$C_4$-alkyl, $C_1$–$C_4$-alkoxy or halogen, $C_1$–$C_4$-alkylsulfonyl, or phenylsulfonyl, carboxyl, $C_1$–$C_4$-alkoxycarbonyl, phenoxycarbonyl, carbamoyl, $C_1$–$C_4$-monoalkylcarbamoyl or $C_1$–$C_4$-dialkylcarbamoyl, each of which is unsubstituted or substituted by $C_1$–$C_4$-alkyl, $C_1$–$C_4$-alkoxy or halogen, or phenylcarbamoyl which is unsubstituted or substituted by $C_1$–$C_4$-alkyl, $C_1$–$C_4$-alkoxy or halogen, or phenyl, each of which is unsubstituted or substituted by $C_1$–$C_4$-alkyl, $C_1$–$C_4$-alkoxy, halogen or nitro, $X^2$ is $C_1$–$C_4$-alkyl or $C_1$–$C_4$-alkoxy, $X^3$ is $C_1$–$C_4$-alkoxycarbonyl or phenylcarbamoyl.

2. The triazolopyridine of claim 1, wherein said $C_1$–$C_{20}$-alkyl radical is substituted with a substituent selected from the group consisting of phenyl, phenoxy, carboxyl or $C_1$–$C_{20}$-alkoxycarbonyl whose alkyl chain may be interrupted by from 1 to 4 ether oxygen atoms and may be substituted by phenyl or phenoxy.

3. The triazolopyridine of claim 1, wherein said phenyl radical is substituted with a substituent selected from the group consisting of $C_1$–$C_4$-alkyl, $C_1$–$C_4$-alkoxy, halogen, nitro or carboxyl.

4. A triazolopyridine as claimed in claim 1, wherein $R^4$ is hydrogen.

5. A triazolopyridine as claimed in claim 1, wherein $R^3$ is $C_1$–$C_4$-alkyl.

6. A triazolopyridine as claimed in claim 1, wherein $R^1$ is $C_1$–$C_{13}$-alkyl or phenyl.

7. A triazolopyridine according to claim 1 of the formula:

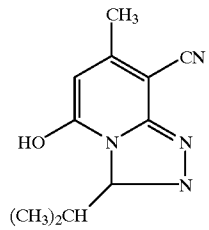

8. A triazolopyridine according to claim 1 of the formula:

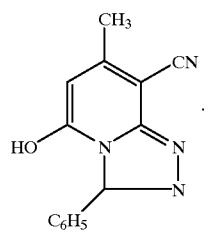

* * * * *